United States Patent
Wash

(10) Patent No.: US 7,857,977 B2
(45) Date of Patent: Dec. 28, 2010

(54) PACKAGING OF FERRIC PYROPHOSPHATE FOR DIALYSIS

(75) Inventor: Lori L. Wash, Redford, MI (US)

(73) Assignee: Rockwell Medical Technologies, Inc., Wixom, MI (US)

( * ) Notice: Subject to any disclaimer, the term of this patent is extended or adjusted under 35 U.S.C. 154(b) by 788 days.

(21) Appl. No.: 11/179,376

(22) Filed: Jul. 12, 2005

(65) Prior Publication Data

US 2007/0012622 A1    Jan. 18, 2007

(51) Int. Cl.
B01D 61/26 (2006.01)

(52) U.S. Cl. .................... 210/647; 424/646; 424/647; 604/403; 604/408

(58) Field of Classification Search ............. 210/645, 210/646, 647; 424/603, 646, 647, 717; 604/28, 604/29, 403, 408
See application file for complete search history.

(56) References Cited

U.S. PATENT DOCUMENTS

| | | | |
|---|---|---|---|
| 2,822,317 A | 2/1958 | Gulesich et al. | |
| 3,275,514 A | 9/1966 | Saltman et al. | |
| 3,367,834 A | 2/1968 | Dexter et al. | |
| 3,537,498 A * | 11/1970 | St Amand | 604/403 |
| 3,686,397 A | 8/1972 | Muller | |
| 3,866,267 A | 2/1975 | Poletti | |
| 4,058,621 A | 11/1977 | Hill | |
| 4,167,564 A | 9/1979 | Jensen | |
| 4,636,412 A * | 1/1987 | Field | 604/408 |
| 4,654,240 A * | 3/1987 | Johnston | 206/524.6 |
| 4,834,983 A | 5/1989 | Hider et al. | |
| 5,063,205 A | 11/1991 | Peters et al. | |
| 5,177,068 A | 1/1993 | Callingham et al. | |
| 5,383,324 A * | 1/1995 | Segers et al. | 53/425 |
| 5,871,477 A * | 2/1999 | Isono et al. | 604/410 |
| 5,895,797 A * | 4/1999 | Hayashihara et al. | 525/95 |
| 5,906,978 A | 5/1999 | Ash | |
| 6,689,275 B1 | 2/2004 | Gupta | |
| 6,779,468 B1 | 8/2004 | Gupta | |
| 6,841,172 B1 | 1/2005 | Ash | |
| 6,896,838 B2 * | 5/2005 | D'Alessio | 264/454 |
| 7,244,795 B2 * | 7/2007 | Agapiou et al. | 526/160 |
| 2004/0028856 A1 * | 2/2004 | Smith et al. | 428/36.6 |
| 2004/0175431 A1 * | 9/2004 | Gupta | 424/604 |
| 2004/0211718 A1 * | 10/2004 | Deguchi et al. | 210/252 |

\* cited by examiner

*Primary Examiner*—John Kim
(74) *Attorney, Agent, or Firm*—Price, Heneveld, Cooper, DeWitt & Litton, LLP

(57) ABSTRACT

A stable packaged bicarbonate solution for use in dialysis treatment and for treating anemia, iron deficiency, or reducing the required dose of recombinant erythropoietin to treat anemia includes a bicarbonate solution into which ferric pyrophosphate is dissolved. The amount of ferric pyrophosphate dissolved in the bicarbonate solution is sufficient to provide a therapeutic effect for the treatment of anemia, iron deficiency or to reduce dose of recombinant erythropoietin needed to treat anemia when the bicarbonate solution is combined with other dialysis components to form a dialysate used for dialyzing a patient. The ferric pyrophosphate is stabilized in the bicarbonate solution by holding the solution in a polyolefin container or container liner, such as a high density polyethylene container or liner.

5 Claims, 1 Drawing Sheet

PACKAGING OF FERRIC PYROPHOSPHATE FOR DIALYSIS

FIELD OF THE INVENTION

This invention pertains to dialysis treatment and more particularly to the packaging of a dialysis bicarbonate solution containing ferric pyrophosphate.

BACKGROUND OF THE INVENTION

Dialysis is a procedure for removing waste products from the blood of a patient when the kidneys are unable to do so on their own. Hemodialysis is a form of dialysis in which waste products are removed from the blood by passing the blood along one side of a semi-permeable membrane and passing a specially formulated solution (i.e., dialysate) along the other side of the semi-permeable membrane. The waste materials that are to be removed from the blood pass with the help of diffusion from the blood of the patient to the dialysis fluid through the permeable membrane.

Another form of dialysis is peritoneal dialysis, in which a dialysate is injected into the patient's abdominal cavity, and the waste materials that are to be removed pass through the membranes of the patient's body into the dialysate which is subsequently drained from the abdominal cavity.

The dialysate is an aqueous solution containing various electrolytes. The dialysate generally comprises dissolved sodium chloride, potassium chloride, calcium chloride, acetate ions, dextrose and other constituents in about the same concentration as normal plasma. Urea, creatinine, uric acid, phosphate and other metabolites normally eliminated by the kidneys diffuse from the blood of the patient into the dialysate until the concentration of these compounds are the same in the blood and in the dialysate. The volume of dialysate fluid used is much greater than the blood volume. The great disparity in volume and the replenishment of dialysate with fresh dialysate ensure that metabolites and excess electrolytes are removed almost completely from the blood.

The dialysate is generally prepared from a dialysate concentrate which contains the sodium ions, potassium ions, calcium ions, magnesium ions, chloride ions, acetate ions and dextrose; a bicarbonate solution; and water. The dialysate concentrate, bicarbonate solution and water are generally combined at, or in close proximity to, a dialysis machine.

Patients receiving regular dialysis treatments for chronic renal failure very frequently are also afflicted with anemia. It is believed that prior to the availability of recombinant erythropoietin, a recombinant DNA version of the human erythropoietin protein that stimulates the production of red blood cells, as many as about 90 percent of all kidney dialysis patients experienced debilitating anemia. A primary cause of anemia in dialysis patients is the inability of the kidneys to produce sufficient erythropoietin to generate adequate amounts of red blood cells. Although erythropoietin therapy stimulates red blood cell production and is very often effective at reducing or eliminating anemia, iron deficiencies are also common among dialysis patients and can result in erythropoietin impairment or resistance. Accordingly, in addition to erythropoietin therapy, it will often be necessary and desirable to deliver iron in a biologically available form to the blood of anemic dialysis patients in order to effectively treat the anemia. Further, there is evidence that iron supplementation can reduce the dose of erythropoietin needed to effectively treat anemia, even for patients that do not have an iron deficiency. This can be very important because recombinant erythropoietin is an expensive drug and can cause mild hypertension and flu-like symptoms. Therefore, it is generally desirable to augment erythropoietin therapy with effective iron supplementation.

It is well known that it is very difficult to treat an iron deficiency with orally administered iron supplements. In general, relatively large doses are needed to achieve a desired therapeutic effect. Further oral administration of iron supplements is known to be commonly accompanied by undesirable side effects including nausea, vomiting, constipation and gastric irritation. For these and other reasons, patient noncompliance is also a common problem.

To overcome the above-described problems with oral delivery of iron, a great deal of effort has been directed to developing iron-containing formulations that are suitable for parenteral administration. Parenterally administered formulations are, in general, aqueous solutions of specific formulation components, in which the solution pH is in the range from pH 4 to pH 8. Parenteral administration encompasses administration by intravenous injection, intramuscular injection, or dialysis.

The formulation of iron-containing compositions for parenteral administration is particularly difficult. The solubility of iron compounds in water is strongly dependent on the pH of the solution and the presence of other formulation components. In general, iron salts are soluble in acidic solutions. Conversely, in basic solutions, unless a chelating agent, such as EDTA is present, iron ions will form insoluble oxides and precipitate from the formulation.

In addition, formulation of iron compounds presents added degrees of difficulty related to the redox chemistries of iron and its ability to catalyze oxidation reactions. With respect to redox chemistries, iron has two common oxidation states, the ferrous or iron$^{2+}$ state and the ferric or iron$^{3+}$ state. In general, iron compounds in which iron is in its ferrous oxidation state are more soluble in water than are iron compounds in which iron is in its ferric oxidation state. In the presence of reducing agents, iron is known to cycle from its ferric to its ferrous oxidation state and vice versa. If the iron composition has lower solubility when iron is in its ferric oxidation state, redox cycling may cause insoluble precipitates to form in the formulation. In addition, iron ions in solution are highly reactive oxidizing agents and catalysts for oxidation of other formulation components. For example, iron ions in solution are known to oxidize other common parenteral formulation components such as dextrose, polysaccharides, amines, and phenols to degradation products having undesirable properties, such as color, biological activities, and toxicities that are different from those of the unoxidized substances.

In U.S. Pat. No. 2,822,317 to Gulesich and Marlino, aqueous iron-ascorbic acid preparations are disclosed, having as essential ingredients a non-toxic ferrous salt, a polyhydric alcohol, l-ascorbic acid, and water. Exemplary of non-toxic ferrous salts are ferrous sulfate, ferrous lactate, ferrous gluconate, ferrous succinate and ferrous complex salts, such as ferrous glutamate and ferrous choline citrates. The polyhydric alcohols are derived from sugars and have from 5 to 6 carbon atoms. Exemplary polyhydric alcohols are mannitol, sorbitol, and arabitol. The l-ascorbic acid may be present in the free acid form or in the form of a derivative. The preparation of this invention containing the essential ingredients with the adjuncts has a pH in the range of from about 2.0 to about 3.5.

With respect to intravenous administration, iron-dextran (INFED®), which may be obtained from Watson Pharmaceuticals, Corona, Calif., is formulated in water containing 0.9% (by weight) sodium chloride for parenteral administration. [Physicians Desk Reference, 59$^{th}$ edition, 2005, pages 3301-

3303]. Iron-dextran is a dextran macromolecule having a molecular weight ranging generally between about 100,000 and about 200,000 to which iron is complexed by both ionic and electrostatic interactions. Iron dextran thus formulated occasionally causes severe allergic reactions, fever and rashes during injection. Parenteral administration intramuscularly is painful and often results in an undesirable discoloration at the injection site. Further, only about half of the iron in iron-dextran is bioavailable after intravenous injection. The fate of the rest is unknown.

Intravenous administration of iron complexes requires venous access and the commercially available intravenously administered iron supplements, such as iron-dextran and ferric gluconate, are relatively expensive and require a great deal of time and skill to administer.

Intraperitoneal delivery of iron-dextran has been used to treat anemia. However, there is evidence that iron-dextran when administered intraperitoneally is stored in macrophages near the peritoneum and could create abnormal changes in the peritoneum.

Other iron preparations which may be administered by injection are taught in U.S. Pat. No. 5,177,068 to Callingham et al., U.S. Pat. No. 5,063,205 to Peters and Raja, U.S. Pat. No. 4,834,983 to Hider et al., U.S. Pat. No. 4,167,564 to Jenson, U.S. Pat. No. 4,058,621 to Hill, U.S. Pat. No. 3,886,267 to Dahlberg et al., U.S. Pat. No. 3,686,397 to Muller, U.S. Pat. No. 3,367,834 to Dexter and Rubin, and U.S. Pat. No. 3,275,514 to Saltman et al., for example. In general, these are formulations of iron bound to polymeric substrates, or chelated by various ligands, saccharates, dextrans, hydrolyzed protein, etc. All have been unsuccessful and/or possess such adverse side effect that practical utilization has not occurred.

It is known to deliver iron to an iron-deficient patient via dialysis using a composition comprising an ionic iron complex. An advantage is that the dialysis treatment delivers iron to the blood at a relatively constant rate throughout the dialysis session. This is because there is negligible free iron in plasma since iron rapidly binds with a apotransferrin to maintain a concentration gradient from dialysate to plasma.

It has been disclosed that preferred forms of iron for use in a dialysate to treat iron deficiency and/or anemia in dialysis patients are noncolloidal ferric compounds, especially ferric pyrophosphate. In particular, it has been proposed to add ferric pyrophosphate to a bicarbonate concentrate which is combined with an acid concentrate and water to provide an iron supplemented dialysate for patients undergoing long-term hemodialysis or peritoneal dialysis for renal failure. Although ferric pyrophosphate is known to be practically insoluble in water, it has been disclosed that ferric pyrophosphate is freely soluble in bicarbonate concentrate. For example, it was disclosed that 1040 milligrams of ferric pyrophosphate may be dissolved in 94.6 liters (25 gallons) of a bicarbonate concentrate to provide an iron pyrophosphate concentration of 11 milligrams per liter in the bicarbonate concentrate. The concentrate may then be combined with the acid concentrate and an appropriate amount of water to generate a dialysate with an iron concentration of 4 micrograms per deciliter.

To prevent stability and/or precipitation problems with dialysate formulations containing iron compounds, admixture of an iron-containing composition with the other formulation components (e.g., bicarbonate concentrate) is completed immediately prior to infusion of the formulation. U.S. Pat. Nos. 6,841,172 and 5,906,978, both to Ash, provide dialysate compositions including an iron complex that is non-polymeric, has a molecular weight less than about 50,000, is soluble in an aqueous medium, and is chemically stable, (i.e., it does not dissociate into iron ions and its other component anions under conditions according to the invention). Exemplary iron complexes of Ash are ferrous gluconate, ferrous sulfate, ferrous fumarate, ferrous citrate, and ferrous succinate. Exemplary of a dialysate composition of this invention is an aqueous solution having dissolved therein sodium (from about 130 to about 150 mEq/L), magnesium (from about 0.4 to about 1.5 mEq/L), calcium (from about 2 to about 4 mEq/L), potassium (from about 1 to about 4 mEq/L), chloride (from about 90 to about 120 mEq/L), acetate (from about 3 to about 5 mEq/L), bicarbonate (from about 30 to about 40 mEq/L), and an iron complex (from about 1 to about 250 microgram/100 mL). Also provided is a dialysate concentrate, prepared for subsequent dilution to a suitable concentration for use as a dialysate, preferably having a concentration about 30 to about 40 times greater than the concentration of the desired dialysate to be administered to the patient. Ash does not teach how to formulate his iron-containing dialysate or dialysate concentrate. The disclosure that the iron-containing dialysate composition may be used without the need to sterilize the iron-containing composition prior to administration indicates that the formulation is completed immediately before parenteral administration of the iron-containing dialysate composition to the patient in order to prevent microbial growth.

U.S. Pat. No. 6,689,275 to Gupta discloses a method of replacing iron losses during dialysis of patients by infusion of a noncolloidal ferric compound, soluble in hemodialysis solutions, during dialysis. A pharmaceutical composition is provided consisting essentially of dialysis solution including a soluble noncolloidal ferric compound, preferably ferric pyrophosphate. A hemodialysis solution is prepared immediately prior to its use by adding ferric pyrophosphate powder from a vial to a bicarbonate concentrate, mixing until dissolution in the bicarbonate concentrate is complete, and then admixing the resulting solution with an acidic dialysate concentrate and water. Alternatively, a pharmaceutical composition of is prepared by adding ferric pyrophosphate powder to an acidic dialysate concentrate, mixing until dissolution in the acidic concentrate is complete, and then admixing the resulting solution with a bicarbonate dialysate concentrate and water.

SUMMARY OF THE INVENTION

A stable packaged bicarbonate solution containing ferric pyrophosphate for use in dialysis treatment and simultaneous treatment of anemia, iron deficiency or the reduction of the dose of recombinant erythropoietin needed to treat anemia has been discovered. The packaged bicarbonate solution includes a bicarbonate solution into which ferric pyrophosphate is dissolved in an amount sufficient to provide a therapeutic effect for the treatment of anemia, iron deficiency, or to reduce the dose of recombinant erythropoietin needed to treat anemia, when the bicarbonate solution is combined with other dialysis components to form a dialysate used for dialysis treatment of a patient. Surprisingly, stability of the bicarbonate solution containing a therapeutically effective amount of ferric pyrophosphate is achieved by holding the bicarbonate solution in a polyolefin container or a container having a polyolefin liner.

These and other features, advantages and objects of the present invention will be further understood and appreciated by those skilled in the art by reference to the following specification, claims and appending drawings.

DESCRIPTION OF THE PREFERRED EMBODIMENTS

Figure 1:
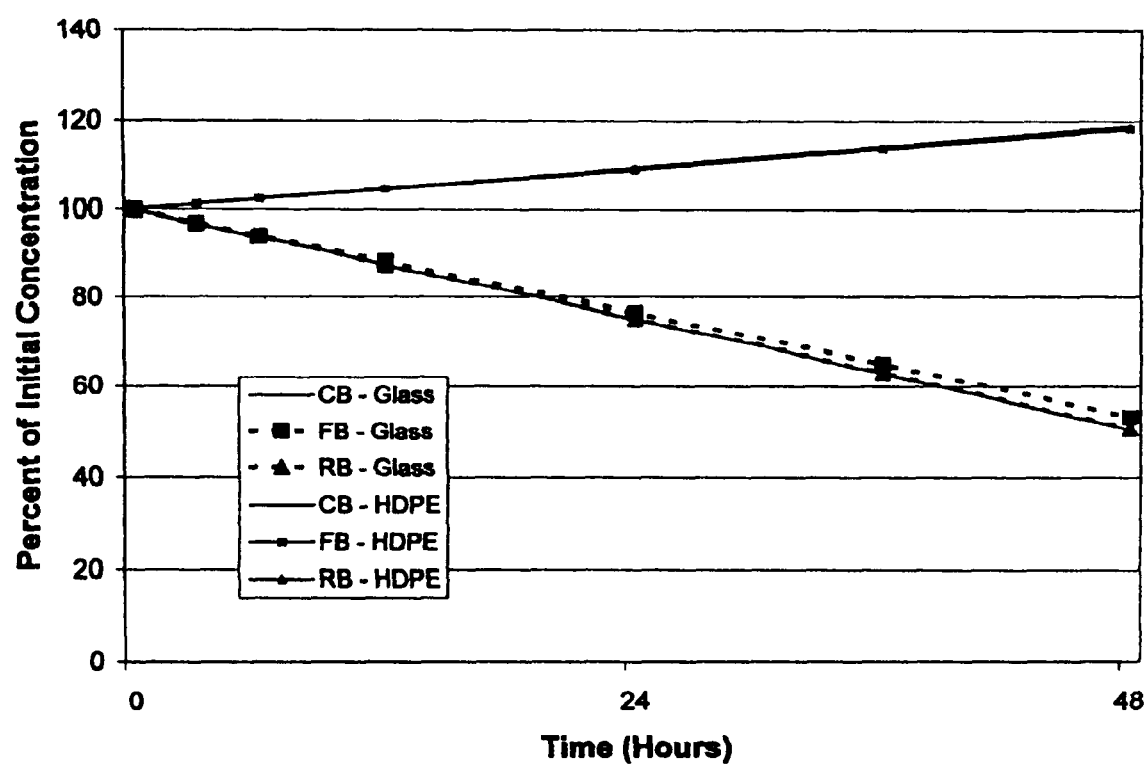
FIG. 1 is a graph showing the change in ferric pyrophosphate concentration with time for different bicarbonate solutions in glass and high density polyethylene containers.

As stated previously, it is generally recognized that iron complexes tend to exhibit instability and/or form undesirable precipitates in solutions including bicarbonate solution used for hemodialysis. For this reason, iron complexes are added in a powdered form to a bicarbonate solution immediately prior to use.

Procedures eliminating the addition of solid components to dialysis solutions at the point of use are desirable because they require fewer steps.

Surprisingly it has been discovered that stability problems with ferric pyrophosphate in a bicarbonate solution can be overcome by utilizing a polyolefin container. More specifically, it was discovered that ferric pyrophosphate dissolved in a bicarbonate solution held in a high density polyethylene container remained in a stable, useable condition, without any detectable precipitation for at least 48 hours. This facilitates preparation of a bicarbonate solution containing ferric pyrophosphate under precisely controlled conditions at a manufacturing facility, and shipment to a remote dialysis treatment facility, thereby eliminating a separate step of adding powered ferric pyrophosphate to the bicarbonate solution in those frequent cases wherein the dialysis patient is anemic and in need of iron supplementation. As a result, the invention provides a safer and more effective dialysis treatment involving iron supplementation to treat anemia. More specifically, the invention allows a technique to treat a dialysis patient with a therapeutically effective amount of ferric pyrophosphate for the treatment of anemia, iron deficiency, or to reduce the dose of recombinant erythropoietin needed to treat anemia, when the bicarbonate solution is combined with other dialysis components to form a dialysate used for dialysis treatment of a patient, by employing substantially the same techniques that are conventionally employed to prepare dialysates that do not contain an iron-supplement. More specifically, water, bicarbonate solution and a dialysis concentrate (typically containing a combination of dissolved sodium ions, potassium ions, calcium ions, acetate ions, dextrose and other conventional constituents) can be combined at or in close proximity to, a dialysis machine, without adding any solid materials. The concentration of ferric pyrophosphate in the bicarbonate solution is typically selected to provide a concentration of ferric pyrophosphate in the dialysate of from about 20 micrograms per deciliter to about 120 micrograms per deciliter after the bicarbonate solution has been combined with any prescribed amount of water and an appropriate dialysis concentrate. This corresponds to an iron concentration of from about 2 micrograms per deciliter to about 12 micrograms per deciliter.

Ferric pyrophosphate ($Fe_4(P_2O_7)_3$, MW. 745.2, CAS 10058-44-3, FePPi) is available in two different forms, pure FePPi (insoluble in water) and soluble FePPi. The second form, soluble FePPi, has been rendered water-soluble by the presence of sodium citrate. It contains 10.5-12.5% iron and occurs as thin apple green, transparent scales, or pearls or granules. Soluble FePPi is very soluble in water. Once dissolved in water or aqueous solutions, the cations ($iron^{+3}$ and $Na^{+1}$) and the anions (pyrophosphate, citrate, phosphate, and carbonate) are detectable using analytical methods known in the art. Phosphate is present in soluble FePPi as a result of hydrolysis of pyrophosphate during manufacture of soluble FePPi. Likewise, carbonate is present in soluble FePPi as a result of absorption of carbon dioxide from the air during manufacture of soluble FePPi. Soluble FePPi is available as a food grade chemical which manufactured by Dr. Paul Lohmann & Co., Emmerthal, Germany.

The following examples are representative of the scope of the invention, and as such are not to be considered or construed as limiting the invention recited in the appended claims.

EXAMPLES

Example 1

The stability of soluble ferric pyrophosphate in three different types of aqueous sodium bicarbonate concentrates (CB, FB, and RB solutions) was monitored during storage at room temperature in glass and high density polyethylene (HDPE) containers. At each test interval (0, 3, 6, 12, 24, 36, and 48 hours), the appearance of the solution, the solution pH, and the concentrations of each of the major anions related to soluble FePPi (pyrophosphate, citrate, and phosphate) were determined. An HPLC assay with conductivity detection was used to determine the concentrations of the anions that were present in each of the bicarbonate solutions at each test interval.

The experimental data showed that the appearance and solution pH of each of the test solutions of soluble FePPi in aqueous bicarbonate concentrates CB, FB, and RB did not change with time during storage in either glass or HDPE containers. No precipitates of iron were detected in any of the test solutions. The citrate concentration did not change in any of the test solutions. However, when solutions of soluble FePPi in aqueous bicarbonate concentrates were stored in glass, a significant decrease in the pyrophosphate concentration was observed (FIG. 1). After 48 hours of storage in glass, the pyrophosphate concentration had decreased to about 50% of its original value. In contrast, when solutions of soluble FePPi in aqueous bicarbonate concentrates were stored in HDPE containers, no change in the pyrophosphate concentration was observed (FIG. 1). The small, apparent increase in pyrophosphate concentration is an artifact of the analytical method.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the doctrine of equivalents.

The invention claimed is:

1. A packaged bicarbonate solution for use in dialysis treatment, comprising:
    a bicarbonate solution into which ferric pyrophosphate is dissolved in an amount sufficient to provide a therapeutic effect for the treatment of anemia, iron deficiency or to reduce the dose of recombinant erythropoietin needed to treat anemia when the bicarbonate solution is combined with other dialysis components to form a dialysate used for dialysis treatment of a patient; and a polyolefin container or a container having a polyolefin liner, in which the bicarbonate solution is contained, the packaged bicarbonate solution being sufficiently stable to provide a ferric pyrophosphate concentration that remains unchanged for at least 48 hours after preparation.

2. The method of claim 1, wherein the polyolefin container or liner is comprised of high density polyethylene.

3. A process for treating anemia, iron deficiency, or for reducing the dose of recombinant erythropoietin needed to treat anemia, during a dialysis treatment, comprising:

preparing a bicarbonate solution suitable for dialysis treatment;

dissolving ferric pyrophosphate in the bicarbonate solution in an amount sufficient to provide a therapeutic effect for the treatment of anemia, iron deficiency, or to reduce the dose of recombinant erythropoietin needed to treat anemia, when the bicarbonate solution is combined with other dialysis components to form a dialysate used for dialysis treatment of a patient;

storing the bicarbonate solution containing the ferric pyrophosphate in a polyolefin container or in a container having a polyolefin liner, the stored bicarbonate solution being sufficiently stable to provide a ferric pyrophosphate concentration that remains unchanged for at least 48 hours after preparation;

combining the bicarbonate solution containing ferric pyrophosphate with a predetermined amount of water and a predetermined dialysis concentrate to form a dialysate; and dialyzing the patient with the dialysate.

4. The process of claim 3, wherein the polyolefin container or liner is comprised of high density polyethylene.

5. The process of claim 3, wherein the iron concentration in the dialysate is from about 2 micrograms per deciliter to about 12 micrograms per deciliter.

\* \* \* \* \*